United States Patent
Koch et al.

(10) Patent No.: US 6,300,136 B1
(45) Date of Patent: Oct. 9, 2001

(54) METHODS FOR DIAGNOSIS AND TREATMENT OF TUMORS IN HUMANS

(75) Inventors: Cameron J. Koch, Aldan; Sydney M. Evans, Swarthmore, both of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/146,401

(22) Filed: Sep. 3, 1998

Related U.S. Application Data

(60) Provisional application No. 60/056,280, filed on Sep. 3, 1997.

(51) Int. Cl.$^7$ ............ G01N 33/48; G01N 33/50
(52) U.S. Cl. ............ 436/64; 436/813; 436/119; 436/120; 435/4
(58) Field of Search ............ 436/64, 119, 120, 436/813; 435/4

(56) References Cited

U.S. PATENT DOCUMENTS

| | | | |
|---|---|---|---|
| 4,940,658 | * | 7/1990 | Allen ............ 435/4 |
| 5,374,560 | * | 12/1994 | Allen ............ 436/129 |
| 5,747,459 | * | 5/1998 | Rowe et al. ............ 514/18 |
| 5,869,456 | * | 2/1999 | Levy et al. ............ 514/19 |

OTHER PUBLICATIONS

Hochwald et al (Ann surg Oncol 1997 Jun.; 4(4):303–9).*
Allison and Shoup, 1983, Anal. Chem. 55:8–12.
Baker et al., 1990, Anal. Biochem. 190:360–365.
Bump et al., 1992, Rad. Res. 132:94–104.
Ellman, 1959, Arch. Biochem. Biophys. 82:70–77.
Evans and Koch, 1994, Rad. Oncol. Invest. 2:134–143.
Fahey and Sundquist, 1991, Adv. Enzym. 64:1–53.
Jocelyn, 1972, *Biochemistry of the sulfhydryl group*, Academic Press, New York (too voluminous to submit).
Koch and Skov, 1994, Int. J. Rad. Biol. Oncol. Phys. 29:345–349.
Koch and Evans, 1996, Int. J. Cancer 67:661–667.
Koch and Skov, 1992, Rad. Res. 132:40–49.
Loh et al., 1990, Rad. Res. 121:98–106.
Meister et al., 1986, J. Amer. Coll. Nutr. 5:137–151.
Post et al., 1983, Biochem. Biophys. Res. Comm. 114:737–742.
Reed, 1990, Ann. Rev. Pharm. Toxicol. 30:603–631.
Standeven and Wetterhahn, 1991, Toxicol. Appl. Pharmacol. 107:269–284.
Tietze, 1969, Anal. Biochem. 27:502–522.
Zheng et al., 1988, Rad. Res. 114:11–27.

* cited by examiner

*Primary Examiner*—Jill Warden
*Assistant Examiner*—Monique T. Cole
(74) *Attorney, Agent, or Firm*—Morgan, Lewis & Bockius, L.L.P.

(57) ABSTRACT

The invention relates to the discovery that the concentration of free cysteine in mammalian tumor tissue is elevated compared with the concentration of free cysteine in non-tumor tissue of the same origin. Elevated levels of free cysteine is, in turn, correlated with resistance of tumors to antitumor therapy such as chemotherapy and radiation therapy. Therefore, the invention further relates to methods of detecting the presence of tumors in mammalian tissues, assessing the resistance of tumors to antitumor therapies as it relates to free cysteine concentration, and to the identification of compounds which affect free cysteine concentration in mammalian tissues.

30 Claims, 6 Drawing Sheets

METHODS FOR DIAGNOSIS AND TREATMENT OF TUMORS IN HUMANS

CROSS REFERENCE TO RELATED APPLICATIONS

This application claims priority, under 35 U.S.C. § 119(e), to U.S. Provisional Application No. 60/056,280, filed on Sept. 3, 1997, which is hereby incorporated herein by reference in its entirety.

GOVERNMENT SUPPORT

This invention was supported in part by funds from the U.S. Government (National Cancer Institute Grant No.CA-49498 and No. CA-56679) and the U.S. Government may therefore have certain rights in the invention.

FIELD OF THE INVENTION

The field of the invention is cysteine levels in mammalian tissues.

BACKGROUND OF THE INVENTION

Low molecular weight thiol-containing compounds play a key role in protecting cells from the toxic effects of ionizing radiation, other free-radical-generating reactions, reactive oxygen species and chemical toxins. The only thiol-containing amino acid, cysteine, is considered to be a relatively minor cellular component in its free form, often reported to be present at concentrations of only a few micromolar in normal tissues (Loh et al., 1990, Rad. Res. 121:98–106). The presence of cysteine in the tripeptide glutathione (GSH) provides a much greater reserve of intracellular thiols than does free cysteine. Total intracellular concentrations of glutathione are typically more than 1 mM and have been reported to be as high as 25 mM in some cells (Post et al., 1983, Biochem. Biophys. Res. Comm. 114:737–742). Intracellular protein thiols comprise an additional 25 mM cysteine, while extracellular proteins, or the extracellular portion of transmembrane proteins, contain predominantly cysteine-cysteine disulfides (cystine) (Jocelyn, 1972, *Biochemistry of the sulfhydryl group*, Academic Press, New York). Enzymes such as glutathione-S-transferase and glutathione peroxidase have evolved to use glutathione, not cysteine, as the nucleophilic acceptor or reductant in cellular protection against toxic xenobiotics (particularly electrophiles) (Reed, 1990, Ann. Rev. Pharm. Toxicol. 30:603–663; Fahey and Sundquist, 1991, Adv. Enzym. 64:1–53).

Studies on the contrasting roles of radiation sensitization by oxygen versus protection by aminothiols have, in similar fashion, emphasized the role of glutathione. Despite this emphasis on the role of glutathione, it remains important to consider the auxiliary role of free cysteine, particularly in protecting cells from damage produced by ionizing radiation. This is because cysteine, due to its neutral charge and smaller size, is expected to have greater access to the negatively charged DNA and, therefore, is expected to provide greater protection from the damaging effects of ionizing radiation. (Zheng et al., 1988, Rad. Res. 114:11–27; Bump et al., 1992, Rad. Res. 132:94–104). However, the prior art does not disclose that tumor cells might have increased concentrations of free cysteine or that this might be a possible mechanism of radiation resistance in tumor cells.

Studies concerning the role of free cysteine in protecting cells from ionizing radiation have been hampered by the fact that cysteine is inherently difficult to measure except as part of the total non-protein sulfhydryl (NPSH) pool (Ellman, 1959, Arch. Biochem. Biophys. 82:70–77). For instance, there are no sensitive biochemical assays for the measurement of free cysteine analogous to the recycling assay for measuring glutathione levels developed by Tietze (1969, Anal. Biochem. 27:502–522). Further, development of more specific assays, based on HPLC, has been hindered by the fact that cysteine and its derivatives are extremely hydrophillic. Thus, cysteine and its derivatives tend to elute with the solvent and salt fronts used in HPLC rendering them difficult to resolve using this method (Allison and Shoup, 1983, Anal. Chem. 55:8–12; Fahey et al., 1983, In: *Radioprotectors and anticarcinogens*, pp. 103–120, Academic Press, New York). Another difficulty hampering the measurement of free cysteine during sample preparation is the presence of enzymes which degrade glutathione, such as y-glutamyltranspeptidase, to cysteine. Indeed, previous studies have suggested that the high cysteine levels observed in tissues such as kidney and liver are artifacts caused by y-glutamyltranspeptidase degradation of glutathione (Standeven and Wetterhahn, 1991, Toxicol. Appl. Pharmacol. 107:269–284).

There has been a long-felt but unfilled need for methods to diagnose tumors in mammals, particularly in the case of tumors which avoid diagnosis using conventional methods. There is also a need to elucidate and measure resistance of tumors to therapies, such as radiation and chemotherapy, and to adjust the therapy for treatment of such tumors. The present invention meets these needs.

SUMMARY OF THE INVENTION

The invention relates to a method of detecting a tumor in a mammalian tissue. The method comprises measuring the concentration of free cysteine in the tissue, wherein a concentration of free cysteine in the tissue higher than about 80 $\mu$M to about 250 $\mu$M is an indication that the tissue bears a tumor.

In one aspect, the mammalian tissue is selected from a group consisting of lung tissue, esophageal tissue, gastro-esophageal tissue, and cervical tissue.

In one embodiment, the mammalian tissue is lung tissue and the concentration of free cysteine in the tissue higher than 200 $\mu$M is an indication that the tissue bears a tumor.

In another embodiment, the mammalian tissue is esophageal tissue and the concentration of free cysteine in the tissue higher than 100 $\mu$M is an indication that the tissue bears a tumor.

In yet another embodiment, the mammalian tissue is gastro-esophageal tissue and the concentration of free cysteine in the tissue higher than 100 $\mu$M is an indication that the tissue bears a tumor.

In yet another embodiment, the mammalian tissue is cervical tissue and the concentration of free cysteine in the tissue higher than 100 $\mu$M is an indication that the tissue bears a tumor.

The invention also includes a method of detecting the growth, remission, or stasis of a tumor in mammalian tissue before, during or after administration of antitumor therapy. The method comprises measuring the concentration of free cysteine in the tissue before, during or after administration of the antitumor therapy. A higher concentration of free cysteine in the tissue compared with the concentration of free cysteine in the tissue before administration of the antitumor therapy is an indication of the growth and/or metastasis of a tumor in a mammal before, during or after administration of antitumor therapy.

In one aspect, the antitumor therapy is selected from a group consisting of chemotherapy and radiation therapy.

The invention also includes a method of detecting the growth, remission, or stasis of a tumor in a mammalian tissue before, during or after administration of antitumor therapy. The method comprises of measuring the concentration of free cysteine in the tissue before, during or after administration of antitumor therapy. The same or a lower concentration of free cysteine in the tissue compared with the concentration of free cysteine in the tissue before the administration of antitumor therapy is an indication of the remission, decrease in size, slowing of growth, reduction or cessation of metastasis, or stasis of a tumor in a mammal before, during or after administration of antitumor therapy.

In one aspect, the antitumor therapy is selected from a group consisting of chemotherapy and radiation therapy.

The invention includes a method of assessing the resistance of tumor cells to antitumor therapy. The method comprises measuring the concentration of free cysteine in the tumor cells and measuring the concentration of free cysteine in non-tumor cells where there is a direct correlation between the concentration of free cysteine in the tumor cells and the resistance of the tumor cells to antitumor therapy such that a higher concentration of free cysteine in a tumor cell compared with the concentration of free cysteine in an otherwise identical tumor cell is an indication that the tumor cell is more resistant to the antitumor therapy.

In one aspect, the tumor cells are in a tumor tissue.

In another aspect, the antitumor therapy is selected from a group consisting of chemotherapy and radiation therapy.

In one embodiment, the antitumor therapy is radiation therapy.

The invention also includes a method of identifying a compound which affects the concentration of free cysteine in a mammalian tissue. The method comprises contacting the tissue with a test compound and comparing the concentration of free cysteine in the tissue with the concentration of free, cysteine in a similar tissue which is not contacted with the test compound where a higher or lower concentration of free cysteine in the tissue contacted with the compound compared with the concentration of free cysteine in the tissue which is not contacted with the compound is an indication that the compound affects the concentration of free cysteine in the tissue.

In one aspect, the mammalian tissue is tumor tissue.

The invention also includes a kit for detecting tumors in a mammal. The kit comprises a set of thiol standards, an acid-chelator solution for preparing a tissue sample, and an instructional material.

The invention includes a kit for measuring the growth, remission, or stasis of a tumor in a mammal before, during or after the administration of antitumor therapy to the mammal. The kit comprises a set of thiol standards, an acid-chelator solution for preparing a tissue sample, and an instructional material.

The invention includes a kit for identifying compounds which affect the concentration of free cysteine in mammalian cells. The kit comprises a set of thiol standards, an acid-chelator solution for preparing a tissue- sample, and an instructional material.

In one aspect, the mammalian cells are in a tissue.

The invention also includes a kit for assessing the radiation resistance of cells. The kit comprises a set of thiol standards, an acid-chelator solution for preparing a tissue sample, and an instructional material.

DETAILED DESCRIPTION OF THE INVENTION

Figure 1:
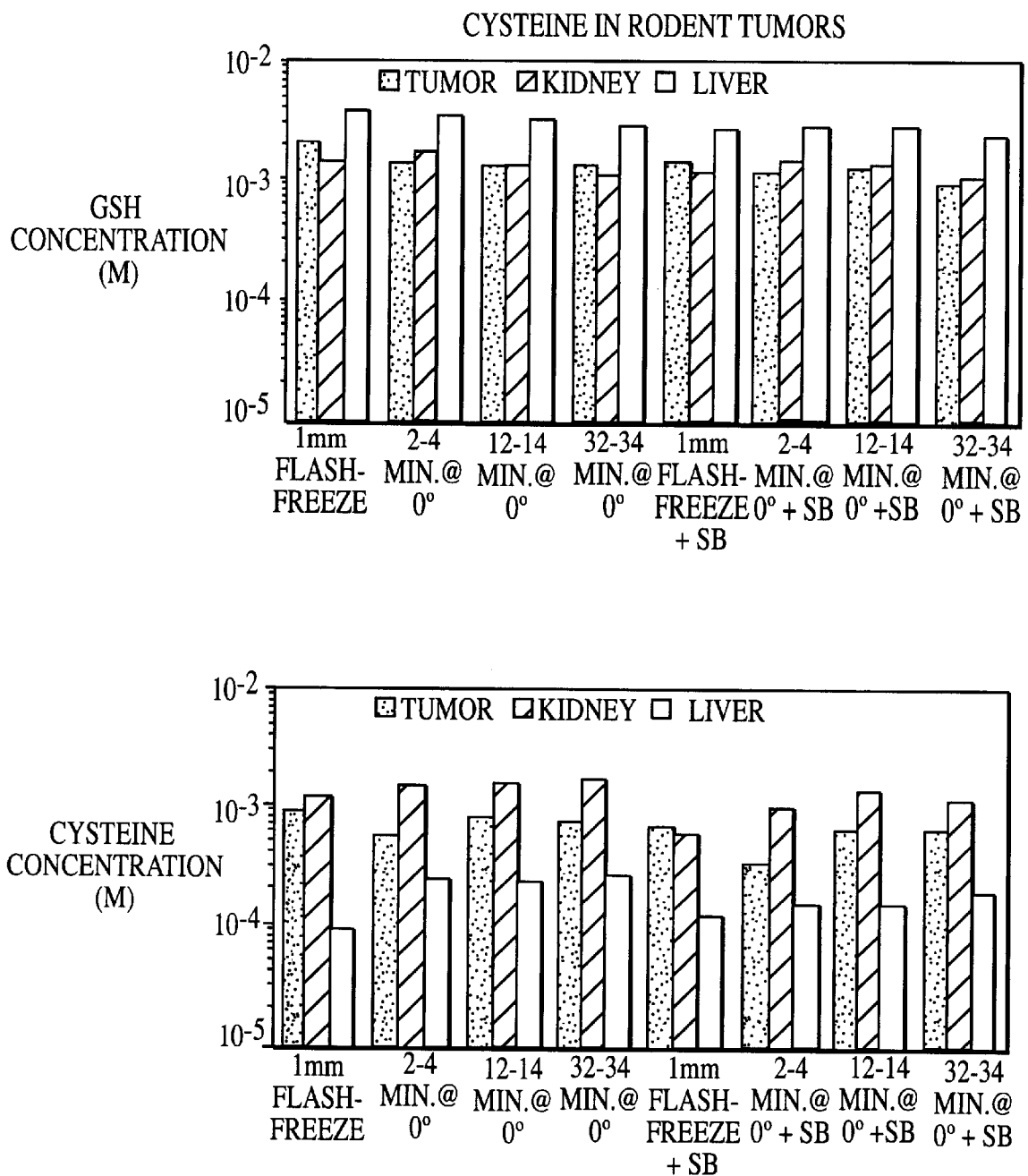
FIG. 1 (comprising two panels) is a graph depicting the effect of tissue preparation methodology on observed tissue cysteine and glutathione concentrations. Biopsies were obtained from tumor (first bar), kidney (second, hatched bar), and liver (third bar) from the same anesthetized animal. Each group of three bars represents a single preparation condition for these three tissues. The biopsies were either flash-frozen in liquid nitrogen (FlashFreeze) or placed in cold acid containing chelators (acid-CH) without 20 mM serine and borate or with 20 mM serine and borate (+SB). The flash-frozen samples were ground in a mortar at dry ice temperature before the frozen, ground powder was added directly to cold acid-CH. From left to right, the samples were flash-frozen, or held in acid-CH for 2–4, 12–14, or 32–34 minutes in the absence of SB or in the presence of SB, respectively, before the sample was minced. The upper panel depicts the concentration of glutathione. The lower panel depicts the free cysteine concentration.

The invention relates to the discovery that the concentration of free cysteine in mammalian tissues is diagnostic for the presence of tumors in the mammal. The invention relates to novel methods of measuring the free cysteine content of mammalian tissues. The methods permit correlation of free cysteine concentration and resistance of tissue to therapies such as radiation and chemotherapy. Further, the invention is useful for the identification of novel compounds which affect cysteine concentration in mammalian tissues. The invention additionally relates to methods of measuring the amount of free cysteine in mammalian tumors to determine the effective dose of therapy to be administered to the tumor and to monitor the dose required to effectuate maximal killing of tumor cells.

The invention is based on the discovery that the concentration of free cysteine in tumor cells, as detected by a sensitive HPLC-based assay method, is much greater than the concentration of free cysteine in non-tumor cells. The greater concentration of free cysteine is likely to provide enhanced protection from the deleterious effects of ionizing radiation and other therapies and may explain the increased radiation resistance typically observed in tumor cells. Thus, the present invention relates to methods for detecting increased resistance to radiation in tissues as expressed by the concentration of free cysteine, within the tissues.

The invention further includes a method for diagnosing the presence of malignant tumors in mammals. The method comprises measuring the free cysteine concentration in mammalian tissue where a free cysteine concentration ranging from about 80 $\mu$M to about 250 $\mu$M is an indication that the mammal has a malignant tumor.

In a preferred embodiment, the mammalian tissue is human pulmonary tissue and a free cysteine concentration of about 200 $\mu$M is an indication that the tissue contains a tumor.

In another preferred embodiment, the mammalian tissue is human esophageal and gastro-esophageal tissue and a free cysteine concentration of about 100 $\mu$M is an indication that the tissue contains a tumor.

In yet another preferred embodiment, the mammalian tissue is human cervical tissue and a free cysteine concentration of about 100 $\mu$M is an indication that the tissue contains a tumor.

The present invention is not limited solely to these tissues or to these specific concentrations of free cysteine. Rather, the invention encompasses other tissues and other concentrations of free cysteine which indicate the presence of a tumor in mammalian tissues.

The present invention is not limited solely to thiol-mediated protection of cells from ionizing radiation. Rather, the invention encompasses any and all cellular processes which may be affected by increasing or decreasing thiol concentration within tissues.

Additionally, in a preferred embodiment, the tumor cells are in a tumor tissue; however, this is not a limitation of the present invention.

Further, the invention includes a method for monitoring the growth, remission or stasis of a tumor by comparing the free cysteine concentration in the tumor cells before, during, or after administration of antitumor therapy to the tumor cells. A higher concentration of free cysteine in the tumor tissue following therapy is an indication of the growth/metastasis of the tumor, while a lower or equal concentration of free cysteine in the tumor tissue following therapy is an indication of a decrease in size, rate of growth, metastasis, and stasis of the tumor tissue.

By "antitumor therapy," as the term is used herein, is meant any means, including but not limited to radiation therapy, chemotherapy, immunotherapy, surgical resection, and the like, used for the treatment of tumors.

By "treating," as the term is used herein, is meant any means of eradicating a tumor and/or causing the tumor to decrease in size, slow its growth, stop its growth, or otherwise alleviating the symptoms associated with the tumor.

The invention includes a method for assessing the resistance of tumor cells to antitumor therapy. The method comprises measuring the concentration of free cysteine within tumor tissue where the concentration of free cysteine is proportional to the resistance of the tumor tissue to antitumor therapies including, but not limited to, radiation therapy and chemotherapy, and where a higher concentration of free cysteine in a tumor cell is an indication that the tumor cell is more resistant to antitumor therapy than an otherwise identical tumor cell having a lower concentration of free cysteine. Alternatively, a lower concentration of free cysteine in a tumor cell is an indication that the tumor cell is less resistant to antitumor therapy than an otherwise identical tumor cell having a higher concentration of free cysteine. Moreover, tumor cells having an equal concentration of free cysteine is an indication that they have substantially similar resistance, if any, to antitumor therapy.

By "free cysteine," as the term is used herein, is meant reduced cysteine amino acid in a cell, i.e., cysteine which is not oxidized and which is not in the form of cystine, and which is not in the form of glutathione or any other aminothiol compound.

By "radiation resistance," as the term is used herein, is meant any increase in the survival rate of cells exposed to a fixed dose of ionizing radiation when compared with cells which are not resistant and which are exposed to the same dose of ionizing radiation. As more fully discussed herein, radiation resistance is a function of many factors including, but not limited to, the ability of cells to effect DNA repair, oxygen concentration, and thiol concentration.

The invention includes a method of identifying compounds which affect the concentration of free cysteine in mammalian tissue. The method comprises contacting a test compound with a mammalian tissue and comparing the concentration of free cysteine in the tissue before and after contact with the test compound. If a compound raises or lowers the concentration of free cysteine in the tissue, this is an indication that the compound affects free cysteine concentration in the tissue.

By the term "contacting," as the term is used herein, is meant any direct contact between a cell or tissue and a compound or agent.

The invention also includes a kit for detecting the presence of a malignant tumor in a mammal by measuring the concentration of free cysteine in the tissues of the animal. The kit comprises a set of thiol standards, an acid-chelator sample buffer and an instructional material.

The invention further includes a kit for measuring the growth, remission or stasis of a tumor in a mammal by measuring the concentration of free cysteine in the tumor before, during and after tumor therapy. The kit comprises a set of thiol standards, an acid-chelator solution for preparing a tissue sample, and an instructional material.

By "growth, remission or stasis of a tumor," as the term is used herein, is meant any change, or no change at all, in the size, location, malignancy, and antitumor therapy resistance of a tumor before, during and after treatment of the tumor by any method or combination of methods including a placebo.

As used herein, an "instructional material" includes a publication, a recording, a diagram, or any other medium of expression which can be used to communicate the usefulness of the composition of the invention for measuring the radiation resistance of cells and tissues. The instructional material of the kit of the invention may, for example, be affixed to a container which contains the thiol standards, or be shipped together with a container which contains the acid-chelator solution. Alternatively, the instructional material may be shipped separately from the container with the intention that the instructional material and the other components of the kit be used cooperatively by the recipient.

The invention includes a kit for identifying compounds which affect the concentration of free cysteine in mammalian cells and tissues. The kit comprises a set of thiol standards, an acid-chelator sample preparation solution, and an instructional material.

The invention further includes a kit for assessing the radiation resistance of tumor cells by measuring the free cysteine concentration in the tumor cells. The kit comprises a set of thiol standards, an acid-chelator sample buffer, and an instructional material.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Measurement of Elevated Levels of Cysteine in Rodent Tumors Compared with Non-tumor Rodent Tissues The experiments presented in this example may be summarized as follows.

Thiol-containing compounds play an important role in protecting cells from the damaging effects of ionizing radiation. Previous studies have emphasized the importance of the tripeptide glutathione, in part, because is the most abundant soluble thiol in cells and because its concentration can be easily assayed. Another important thiol-containing compound, cysteine, is more difficult to quantitate than glutathione, and is much less abundant with reported concentrations only 1–10% of that of glutathione in most normal tissues and tissue culture cells. Using an electrochemical method (e.g., oxidation of the functional sulfhydryl group) which allows the direct assay of thiols after acid extraction of cells or tissue, the data disclosed herein confirm the above indicated distribution of glutathione and cysteine in cells and normal tissues. However, in several rat and mouse tumors grown in vivo, a much higher proportion of cysteine, sometimes exceeding the millimolar concentrations often found for glutathione, has been demonstrated herein. These results, have important implications for predicting tumor radiation resistance since cysteine is a much better radiation-protecting agent than glutathione. Since thiols and oxygen have interacting and opposite effects of the net radiation response, high cysteine levels should directly increase the proportion of radiation-resistant cells in tumors. Thus, determination of high cysteine levels in cells is a predictor of the radiation resistance of the cells, and is therefore useful for determining the dose of radiation and/or the type of therapy, required to effect maximum killing of the tumor cells.

The Materials and Methods used in the experiments presented in this example are now described.

Sample Preparation

Sample preparation for thiol analysis involved a simple homogenization and precipitation of macromolecules in cold acid containing chelators (acid-CH) to inhibit thiol oxidation (Koch and Skov, 1994, Int. J. Rad. Biol. Oncol. Phys. 29:345–349). The composition of this mixture resulted in a final concentration of 50 $\mu$M sulfosalicylic acid and 50 $\mu$M each of ethylenediaminetetraacetic acid, diethylenetriaminepentaacetic acid and diethyldithiocarbamate. After high-speed centrifugation to remove macromolecular precipitates (5 minutes in a Fisher 59A microcentrifuge at maximum speed), the visually clear supernatants were assayed directly or after additional dilutions in acid-CH. Small volumes of the acid-CH supernatant were used directly to analyze for glutathione by the Tietze method (Tietze, 1969, Anal. Biochem. 27:502–522; Baker et al., 1990, Anal. Biochem. 190:360–365).

Cells

V79-WNRE Chinese hamster fibroblasts were obtained from Dr. J. D. Chapman, Fox-Chase Cancer Center, Philadelphia, PA; EMT6-Ro cells were obtained from Dr. E. M. Lord, University of Rochester; Chinese hamster ovary cells were obtained from Dr. J. E. Bigalow, University of Pennsylvania; rat 9L glioma cells were obtained from Dr. K. T. Wheeler, Bowman Gray University; and Morris 7777 hepatoma cells were obtained from the ATTC (Rockville, Md.). These cell lines have been described previously (Koch and Evans, 1996, Int. J. Cancer 67:661–667). All cell lines were grown in Eagle's minimal medium, with standard antibiotics and 12% serum. Bovine calf serum was used for the 9L cells and fetal bovine serum was used for all other cells.

Tumors were grown subcutaneously in their appropriate host as follows: 9L glioma in male Fischer rats; Morris 7777 hepatoma in male Buffalo rats; EMT6 mammary sarcoma in BALB/cBYJ female mice; KHT sarcoma tumors in C3H/HeJ female mice; and FSaII fibrosarcoma tumors in C3H male mice. 9L glioma tumors were also grown in the epigastric location, with isolated blood supply as described in Evans and Koch (1994, Rad. Oncol. Invest. 2:134–143)

Thiol Measurement

Tumors were prepared as described by Evans and Koch (1994, Rad. Oncol. Invest. 2:134–143). Biopsy specimens were made in the anesthetized animal before the tumor or other organ was excised and the specimens were placed directly into 2-ml screw-cap polypropylene tubes, each containing 750 $\mu$l of ice-cold acid-CH. The weight of the acid-containing tubes was recorded before and after addition of the biopsy specimen to determine the biopsy specimen mass. Blood (15–25 $\mu$l) was added directly to acid-CH. Samples were minced, using fine scissors, and allowed to stand on ice for 10 minutes then centrifuged. The effects of additional homogenization using a Polytron or rotating pestle were studied and additional homogenization was found to be unnecessary. In some experiments, tumor biopsies were disaggregated to single cell suspensions (Evans and Koch, 1994, Rad. Oncol. Invest. 2:134–143) and thiols were measured in the initial cell suspension and then in the supernatant and pellet after centrifugation of cells. Thiols present in media, cells in suspension, etc., were analyzed in the same fashion, after acidification via the addition of an equal volume of twice-concentrated acid-CH. Cell pellets were resuspended directly into acid-CH.

Standards were prepared individually at high concentration (25–50 mM) in 0.1 M formic acid with 100 $\mu$M diethyldithiocarbamate (pH approx. 3.5) and stored at 4° C. for up to 1 month. Their thiol content was verified by titration with 5, 5'-dithiobis-2-nitrobenzoic acid at pH 7.5, assuming a molar absorption coefficient of 13,600. The concentrated standards were diluted in acid-CH before use, typically to 5 $\mu$M cysteine+10 $\mu$M glutathione. The standards were stable, even at these low concentrations, for at least 1 week.

HPLC

Injections were made with a Waters (Millford, Mass.) autoinjector (712 WISP).

A Waters 460 Electrochemical Detector, set for oxidation at approximately+0.2 V relative to a silver chloride reference, was used. The oxidizing electrode was either silver or gold, coated with mercury (Koch and Skov, 1994, Int. J. Rad. Biol. Oncol. Phys. 29:345–349). The instrument was usually set at its lowest sensitivity (i.e., 200 nA producing 100 mV) and the signal was recorded on a Houston Instruments (Houston, Tex.) chart recorder. Detection limits were of the order of 2–5 pmol thiol. HPLC columns were Alltech "Adsorbosphere," C-18 with 7$\mu$bead size, 250 mm length (Alltech Associates, Deerfield, Ill.). All separations were performed at room temperature; the mobile phase was 0.1 M phosphoric acid with 5 mM heptane sulfonic acid in water with variable methanol, pH 2.0, 0.9 ml/minute. Mobile phase was continuously purged with helium. The column life was not long at pH 2.0, which is the absolute minimum specified by the manufacturer, and over a period of about 2 months it was necessary to decrease the methanol concentration from 10% to 0% to allow adequate resolution of cysteine.

Numerous checks were made to determine the stability of the thiol measurements at various points in the procedure. Some change in thiol concentration was observed (typically a small increased in cysteine) if a significant time (e.g., 10–30 minutes) was allowed before placing the biopsy specimen into cold acid; however, no difference could be detected between immediate addition and small delays of 1–3 minutes. No differential thiol loss was observed under any conditions once the sample was in cold acid-CH; all of the other variables tested (e.g., time between acid-CH addition and mincing, time between mincing and homogenization, time between mincing and high-speed centrifugation, time between centrifugation and HPLC assay) had no significant effect on thiol recovery. To test for artifactual production of cysteine via $\gamma$-glutamyltranspeptidase, a more stringent test was devised, even though this may be impractical for routine biopsy procedures. Tissue was removed from an anesthetized animal and frozen directly in liquid nitrogen. The tissue was ground with a mortar at dry-ice temperature and the frozen powder was then added directly to cold acid-CH. Since $\gamma$-glutamyltranspeptidase is inhibited by serine and borate at high concentration (20 mM), comparisons were also made between tissue prepared in acid-CH alone compared with acid-CH containing serine and borate (+SB).

The Results of the experiments presented in this example are now described.

Cysteine Thiol Measurements Were Not Due to Breakdown of Glutathione

Detailed control experiments to eliminate artifactual production of cysteine from $\gamma$-glutamyltranspeptidase, or perhaps other enzymes, exhibited minimal evidence for any effect when using the methods described herein (FIG. 1). In this experiment, tissue biopsies obtained from tumor, kidney or liver were either flash-frozen in liquid nitrogen or stored in cold acid-CH for up to 30 minutes before mincing. Frozen tissue was ground in a mortar at dry-ice temperature before being added directly to acid-CH. For half of the samples the acid-CH was supplemented with 20 mM each of serine and borate (FIG. 1). This experiment was repeated twice, without the serine-borate, with the time between sample collection and mincing varying up to 2 hours. Similar results were obtained; that is, there was little effect observed upon varying the time between sample collection and mincing.

Figure 2:
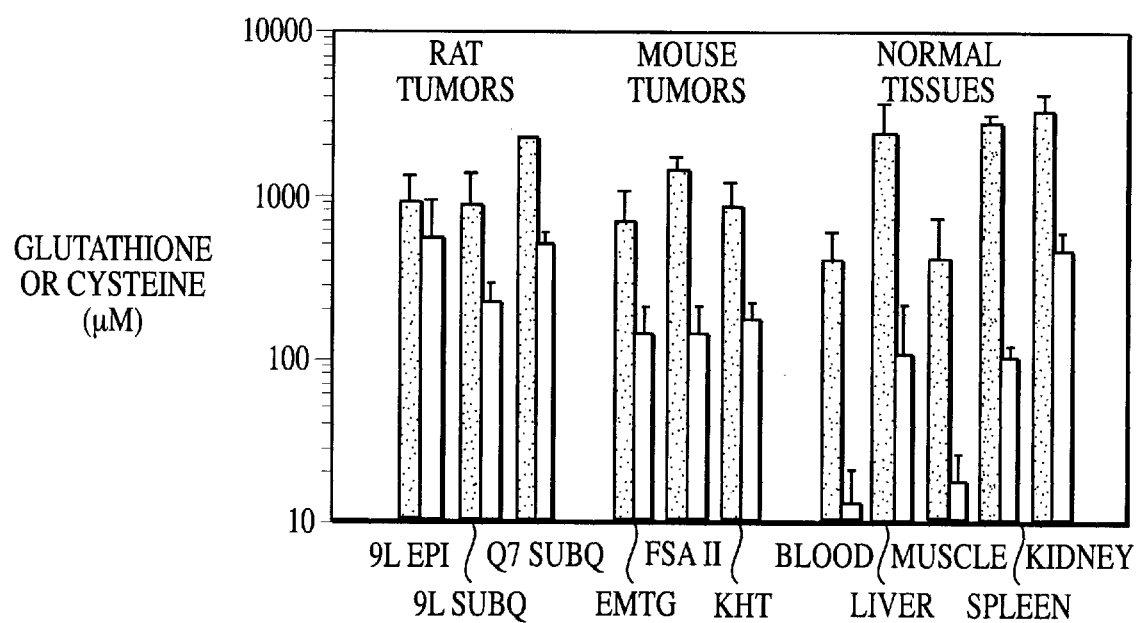
FIG. 2 is a graph depicting the glutathione and cysteine concentrations present in tumor and normal rodent tissues. "Normal" tissue samples were generally from tumor-bearing animals. "Concentrations" were calculated by multiplying the measured thiol concentration by the mass of tissue plus acid divided by tissue mass. There is a negligible error in assuming that the density of tissue is 1.0, but it is not known if the thiols are uniformly distributed within the tissue sample (e.g., some fraction of the tissue will always be blood). Error bars represent standard deviations, with 5–20 samples per tissue (obtained from different animals). With the exception of kidney, cysteine concentrations are typically less or much less than 100 $\mu$M and less than 5% of the glutathione concentration in normal tissues. In dramatic contrast, all rodent tumor tissues had greater than 200 $\mu$M cysteine and the percentage of cysteine to glutathione varied from 20% to nearly 100%.

Tumor Tissue Demonstrated Increased Levels of Cysteine Compared with Normal Tissue Assays of normal and tumor tissue glutathione concentrations by the electrochemical method yielded values which were consistent with previously published results (FIG. 2). Liver, kidney and spleen had glutathione concentrations greater than 2 mM, while whole blood and muscle had much lower values in the order of about 300 $\mu$M. Of course, blood contains mostly serum and does not accurately reflect, for example, the concentration of glutathione in red blood cells. With the exception of kidney, cysteine concentrations were typically about 5% of the glutathione concentrations in the same tissue; in kidney, cysteine was present at about 400 $\mu$M, or 20% of the glutathione value (FIG. 2). Little difference was observed in these normal tissues between mouse and rat or between different strains of either rodent. The liver samples occasionally contained 1 or 2 small peaks in addition to cysteine and glutathione. This seemed to vary with the preparation and with the "age" of the column and detector (i.e.,time since amalgamation of the electrode with fresh mercury). Since the electrochemical detector cannot be assumed to be specific for thiols, supernatant samples were neutralized, treated with thiol-reactive chemicals, then re-acidified and analyzed again, accounting for the volume changes. Dithiobis-2-nitrobenzoic acid, iodoacetic acid, iodoacetamide, and N-ethylmaletimide (NEM) all eliminated the known thiol peaks (cysteine and glutathione) in both standards and samples, but only NEM did not react within the electrochemical system to produce significant perturbations in baseline stability. Use of NEM in this way indicated that the extra peak(s) from liver samples did not contain thiol, with the possible exception of a very minor component which had a retention time consistent with cysteamine.

Figure 3:
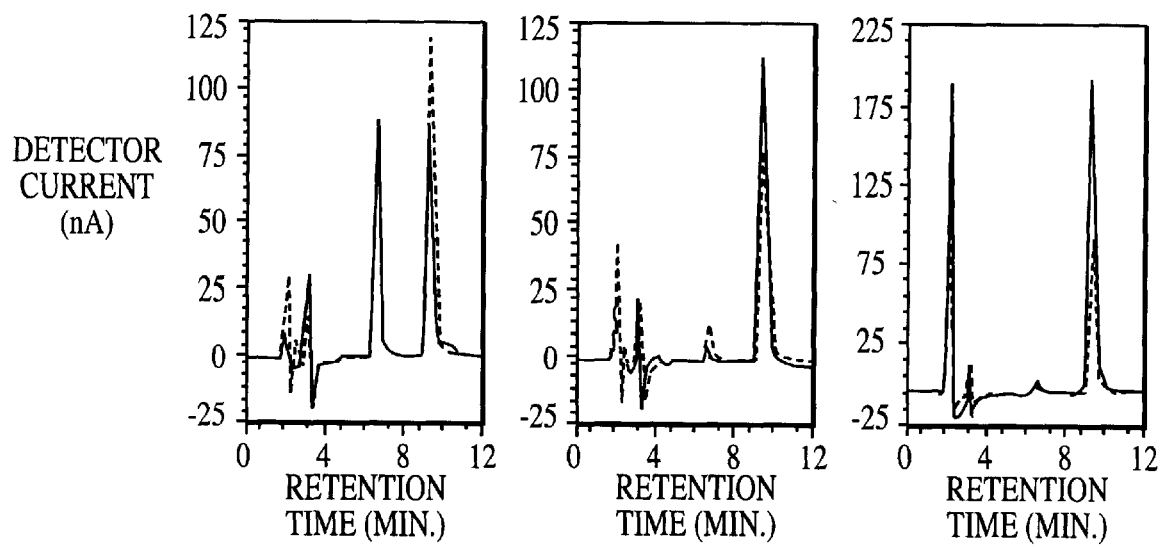
FIG. 3 is a graph (comprising three panels) depicting the HPLC profiles of normal and tumor tissue obtained from a single Buffalo rat bearing a subcutaneous Morris 7777 hepatoma tumor. In the left panel, a standard (5 mM cysteine+10 mM glutathione, solid line) is compared with the tumor sample (dashed line). In the center panel, rat liver (solid line) is compared with rat spleen (dashed line). In the right panel, rat muscle (solid line) is compared with whole blood (dashed line). Thiol concentrations have been found to be linearly related to peak height, but samples were diluted to reduce concentrations to values similar to standards. The peaks at times less than four minutes are due to the large concentrations of ions which elute at times similar to the solvent fronts. For calculated concentrations see Table 1. Cysteine elutes between about 6 and about 7 minutes and glutathione between about 9 and about 10 minutes after injection.

A variety of implanted rodent tumors exhibited glutathione levels in the millimolar range, similar to many normal tissues, but the Morris 7777 hepatoma, like its tissue of origin (liver), had substantially higher glutathione values (2–5 mM, FIG. 2). Cysteine concentrations, in all tumor tissues studied, were at least 20% of those of glutathione (FIG. 2). The highest relative values were seen in the 9L rat glioma, grown in epigastric isolate location (Evans and Koch, 1994, Rad. Oncol. Invest. 2:134–143), with cysteine concentrations sometimes exceeding glutathione levels of 1mM. Most Morris 7777 hepatoma tumors had average cysteine concentrations of about 500 $\mu$M, with occasional values of more than 1 $\mu$M (FIGS. 2, 3).

Representative HPLC thiol profiles of tissues from a single rat, bearing a 7777 hepatoma, illustrate the results discussed above (FIG. 3), and the thiol concentrations calculated from these profiles are shown in Table 1. Although normal tissues obtained from non-tumor-bearing animals were not examined routinely, blood samples were similar in the tumor-bearing and non-tumor-bearing groups. HPLC profiles of human blood samples, using 10 $\mu$l fingerstick samples, were very similar to those of the rodents, with slightly lower cysteine levels. Although the profiles shown are from a single animal (to compare with the values in Table 1), this procedure was used for all analyses.

TABLE 1

Analysis of Data From HPLC Profiles From a Single Buffalo Rat

| Sample | (dil) | $\mu$M CySH | $\mu$M GSH | $\mu$M GSH (Tietze) |
|---|---|---|---|---|
| Standard | — | 5.0 | 10.0 | 10.0 |
| Q7 tumor | (0.0022) | 1,760.0 | 6,660.0 | 7,200.0 |
| Rat liver (Buffalo) | (0.0043) | 100.0 | 3,243.0 | 4,730.0 |
| Rat spleen (Buffalo) | (0.0043) | 211.0 | 2,239.0 | ND |
| Rat muscle (Buffalo) | (0.02) | 30.3 | 595.0 | ND |
| Rat blood (Buffalo) | (0.05) | 5.5 | 464.0 | 436.0 |
| Rat liver (Fischer) (n = 3) | — | 141.0 | 2,220.0 | 2,150.0 |
| 9 L tumor (n = 3) | — | 686.0 | 1,270.0 | 1,630.0 |

Analysis of typical data from profiles shown in FIG. 3, for cysteine and glutathione values were measured by HPLC, and comparison with glutathione concentrations was measured by Tietze assay (Buffalo rat bearing Morris 7777 hepatoma). The last two lines of the Table illustrate liver and tumor data summarized from three Fischer rats bearing 9L glioma tumors. The dilution factor is the weight of the tissue mass divided by the weight of the tissue plus acid-CH mass.

Effect of Biopsy Technique on Cysteine Measurement

Various biopsy techniques have been employed including removal of a small piece of excised tissue, core biopsy, fine needle aspirate, and disaggregating cells from a tumor sample using a mixture of protease, collagenase and DNAase, in isotonic buffer (Evans and Koch, 1994, supra). A comparison of the excising tissue method with the tumor disaggregation method demonstrates that there is a significant loss of thiols during the tumor cell disaggregation method (Table 2). In this experiment, tumor tissue originally contained about 700 $\mu$M cysteine and 1,300 $\mu$M glutathione. After disaggregating 0.5 gram of tissue, the resulting cell suspension (cells, enzyme and medium) contained 8 $\mu$M cysteine but only 2.2 $\mu$M glutathione. Considering the dilution involved (a factor of 60), virtually all of the cysteine was accounted for, but 85% of the glutathione had been lost. Without wishing to be bound by theory, it may be that glutathione was partially converted to cysteine and that both thiols oxidized to a similar extent. After centrifugation, virtually all of the cysteine remained in the supernatant and most of the glutathione pelleted with the cells. The fine needle aspirate method yielded low overall thiol levels probably because of the presence of significant blood components. Excisional biopsies yielded similar thiol concentrations compared with core biopsies.

TABLE 2

Analysis of Cysteine and Glutathione Levels In Whole Tissue or in the Various Solutions and Suspensions Involved with Disaggregating a 9 L Glioma Tumor into Single Cells

| Sample (dil) | $\mu$M CySH | $\mu$M GSH | $\mu$M GSH (Tietze) |
|---|---|---|---|
| Tumor biopsy[1] | 700.0 | 1,300.0 | 1,450.0 |
| Disaggregate 0.5 g of 9 L tumor; total volume at end of procedure is 30 ml | | | |
| Tumor cell suspension | 8.3 | 2.2 | 2.6 |
| Supernatant of centrifuged cells | 8.5 | 0.4 | ND |
| Cells resuspended at same density | 0.2 | 1.5 | 1.6 |

[1]Note that the concentrations following disaggregation should be multiplied by 60 to compare with the original tumor biopsy.

Elevated Cysteine Levels Were not Observed When Tumor Cells Were Grown in Vitro

The high cysteine levels and low glutathione:cysteine ratios found in the tumors were not necessarily a characteristic of the cells themselves, but, rather, of their environment. This is suggested by the fact that the same tumor cells, when grown in tissue culture and directly precipitated in acid-CH, did not contain similar thiol values as tumor cells grown in vivo (Table 3).

TABLE 3

Analysis of Cysteine and Glutathione Levels in Tissue Culture Cells (Approximately 1.5 × 10$^6$ cells per 5 cm dish)

| Sample | $\mu$M CySH | $\mu$M GSH |
|---|---|---|
| V79-WNRE Chinese hamster fibroblasts | 272.0 | 4,375.0 |
| Chinese hamster ovary cells | 110.0 | 5,550.0 |
| EMT6-Ro mouse mammary carcinoma | 465.0 | 5,550.0 |
| Morris 7777 rat hepatoma | 47.0 | 18,000.0 |
| 9 L rat glioma | 555.0 | 6,000.0 |

The approximate cell volumes used to compute thiol concentration were 800 fL for the V79 fibroblasts and CHO cells and 2,000 fL for the other cells.

Correlation of Cysteine Measurements to Previous Studies

The tissue glutathione concentrations disclosed herein appear to be on the low end of the relatively large range of previously measured values (Tietze, 1969, Anal. Biochem. 27:502–522; Meister et al.,1986, J. Amer. Coll. Nutr. 5:137–151). Although the reasons for this observation are unclear, certainly, the relative ranking of glutathione concentrations in the various tissues studied (liver> kidney~ spleen> tumor> muscle or blood) is similar to that methods disclosed herein. Studies reporting cysteine values determined from normal tissues are quite rare in the prior art, but the observations disclosed herein are similar on an absolute and relative basis to previous published measurements (Meister et al, 1986, supra). Thus, it appears that the facile tissue preparation and thiol extraction methods described herein are reliable, particularly since additional extraction (e.g., with Polytron) was without effect. The data in FIG. 1 may be interpreted as demonstrating a small increase in liver and kidney (but not tumor) cysteine for the flash-frozen versus the normal typical biopsies. However, the powder from the flash-frozen portion was used for both the control acid-CH and the serine-borate acid-CH samples, in contrast to the individual biopsies used for all other samples. Thus, any intra-tissue heterogeneity would have a high degree of correlation for the flash-frozen case. In two other similar experiments, but without the serine-borate variable, the flash-frozen tissue from liver and kidney also tended to have slightly lower cysteine levels than the non-frozen biopsies but with a similar degree of variability overall. Without wishing to be bound by theory, it may be that the lower cysteine value of the flash-frozen non-tumor samples is due to a gain in the cysteine levels of the non-frozen tissues (perhaps caused by transpeptidase activity) or from a loss of reduced cysteine, which is the only form detectable by this assay, in the frozen powder preparation (perhaps caused by oxidation). Nonetheless, the errors involved are small, considering the potential problems associated with immediate freezing and grinding of tissue biopsy samples. None of the data disclosed herein suggest such an effect for the tumor samples assayed.

Additionally, there has been no effort to remove blood components from the biopsies. Indeed, it is unclear how this may be accomplished in a simple assay, and as was shown, tumor cell disaggregation leads to both cysteine and glutathione loss (Table 2). Since blood contains very low cysteine, contamination of the biopsies by blood would cause an apparent decrease in the actual cysteine values within the tissues.

A major advantage of the electrochemical detection method described herein is that the sample is prepared and analyzed in a cold acid environment which preserves the thiols in their native state. Furthermore, the relatively low concentration of sulfosalicylic acid may simply be neutralized to assay for GSH using the Tietze method (1969, supra) as described in Baker et al. (1990, Anal. Biochem. 190:360–365). Although the resulting salt seems to inhibit the Tietze assay slightly, this may be easily corrected for by preparing standards in an identical manner. The HPLC assay has a greater dynamic range and a higher sensitivity for both cysteine and glutathione than does the Tietze assay (for GSH only), but usually the same sample can be assayed by both methods. Good agreement was demonstrated between both of these thiol detection methods for GSH (Table 1). This suggests that thiol oxidation must be minimal with the present procedure since oxidized and reduced glutathione are not differentiated using the Tietze assay, but only reduced thiols are measured by the electrochemical method. Further, the data disclosed herein demonstrate that no measurable thiol-disulfide exchange takes place in acid-CH at 4° C., and that possible extraneous sources of cysteine, such as proteins, are rapidly removed by the acid precipitation of macromolecules using the method described herein. Alternative methods require derivatization of thiols with other detectable chemical groups, at higher pH and temperatures, and these conditions could allow thiol metabolism, oxidation, or exchange to take place.

Effects of Various Factors on Cysteine Measurements

Despite the potential advantages of the technique described herein, there are several steps of the tissue-harvesting procedure where timing may be critical to prevent oxidation or anomalous production of cysteine clue to glutathione or protein hydrolysis or exchange reactions. Accordingly, the following variables were examined: time after tissue excision; time before immersion in acid; time in acid before mincing; time before tissue homogenization; time before removal of the acid-precipitated material; and overall time of the assay. Of these, only the time after tissue excision and before immersion of the biopsy sample in cold acid-CH had any effect, and even this was minor, with small increases in cysteine being observed. This time-dependent effect was possibly due to induction of hypoxia in the tissue sample. The data disclosed herein suggest that the time between tissue excision and immersion in acid-CH should preferably be limited to less than 3 minutes but such a requirement is neither critical nor technically demanding.

Various biopsy techniques have been attempted, and it appears that representative thiol concentrations are not obtained from fine needle aspirates or from cells disaggregated from a tumor sample using a mixture of enzymes (Table 1). In the case of fine needle aspirates, this is probably due to the unavoidable dilution by blood components. Indeed, fine needle aspirates often contain a highly disproportionate fraction of red blood cells and other whole blood components. For the enzymatic disaggregation of cells obtained from tumors (Table 1), several factors may be important in explaining the low cysteine concentrations observed herein for tumor cells. First, it is impossible to obtain the same mass of final cells as the initial tissue sample (10% would be an outstanding recovery). Thus, the cell population which results from the enzymatic procedure may not fully represent the cells in the entire excised tissue sample. Secondly, there is loss of intracellular components due to a lack of normal medium and serum components in the enzyme mixture. A third factor is that intracellular components may be lost due to membrane damage. The loss of thiols from cells subjected to degradative enzymes is not limited to tumor preparations. For cells in tissue culture, significant loss of cysteine and even glutathione is found following the common procedure of trypsinization and centrifugation of cells. Thus, a minimum of core or excisional biopsy is required for accurate thiol analysis.

The methods described herein do not result in the artifactual production of cysteine, as suggested by Standeven and Wetterhahn (1991, Toxicol. Appl. Pharmacol. 107:269–284). Since tumor cysteine remains using the technique disclosed herein even after immediate flash-freezing of tissue in liquid nitrogen or with tissue homogenization in the presence of serine and borate, it is clear that the results disclosed herein correctly represent endogenous tumor cysteine levels. Previous studies have suggested that there might be an anomalous production of homocysteine in tumors. However, the present invention verified that homocysteine elutes after glutathione under the present HPLC conditions and does not, therefore, account for the results obtained herein. In fact, the only thiol tested which elutes close to cysteine is N-acetylcysteine. And this compound, which is not an endogenous thiol, elutes sufficiently before cysteine such that it is separable therefrom under the methods disclosed herein. Moreover the γ-glutamyl-cysteine precursor to glutathione elutes just before glutathione and is also easily differentiated from cysteine as well.

Without wishing to be bound by theory, many factors are involved in the net radiation response of tumors and normal tissues. One major modifying factor influencing the radiation response is the intracellular radiation-chemical environment (Koch, 1983, In: *Radio receptors and anticarcinogens*, pp. 275–296, Academic Press, New York). For example, the absence of oxygen leads to a highly increased radiation resistance: to kill the same fraction of cells, a three-fold greater radiation dose is required for anoxic cells compared with aerobic cells. However, this "oxygen effect" is not an all-or-none phenomenon. For otherwise constant conditions, there is a characteristic increase in radiation resistance as the oxygen concentration, [$O_2$], decreases over a roughly two decade range. Radiation resistance may be described as the dose for a constant effect (Koch and Skov, 1992, Rad. Res. 132:40–49), and its dependence on oxygen concentration can be described mathematically as:

$$Dose = (C1 + C2) - C2 \times \frac{[O_2]}{([O_2] + P)} \qquad (e1)$$

In this equation, the dose for an effect of interest (e.g., 10% survival) depends not only on the oxygen concentration, but also on constants, C1 and C2, and the value of P. The dose would vary between (C1) in fully sensitive (i.e., high oxygen) conditions and [C1 +C2] in fully resistant (anoxic, zero oxygen) conditions. C2 is typically twice as large as C1 for mammalian cells, leading to the three-fold difference in radiation response referred to previously herein. The factor P in the denominator is not a constant, in that it varies with the type and quantity of aminothiol radiation-protecting molecules present (Koch, 1983, supra; Koch and Skov, 1992, supra). Thus, the range of oxygen concentrations over which radiation resistance varies most strongly is directly related to the endogenous level of radioprotective thiols. Another way of thinking of this is that P represents a concentration of oxygen that can compete on an equal basis with the endogenous protecting molecules present.

Previous studies have focused on the importance of glutathione because it has always been measured as the dominant cellular thiol. However, direct comparisons of the relative efficiency of various aminothiol radiation protectors at intermediate oxygen levels have shown that cysteine is greatly superior to glutathione in protecting against radiation-induced DNA double stranded breaks (Bump et al., 1992, Rad. Res. 132:94–104). This is in accordance with other studies in several experimental systems which have shown that neutral or positively charged thiols are greatly superior to glutathione as radio-protective molecules (Zheng et al., 1988, Rad. Res. 114:11–27). Therefore, an undue emphasis has been placed on glutathione because other thiols, such as cysteine, are present in lesser amounts compared with glutathione and are technically difficult to quantify. The results disclosed herein indicate that cysteine may play an even more significant role than previously thought. Although there are no studies which address this question for clonogenic survival of irradiated cells, it is expected that 1 mM cysteine would shift the P value to substantially higher values thereby enhancing the importance of hypoxia in determining radiation therapy resistance.

Further, to date, a mechanism leading to the high levels of cysteine in tumors disclosed herein has not been elucidated.

Example 2
Measurement of Elevated Levels of Cysteine in Human Lesions

The experiments presented in this example may be summarized as follows.

Essentially, all human tumors examined demonstrated significantly elevated free cysteine levels compared with non-tumor tissue of the same origin. These results were obtained in all human tumors obtained to date including lung, esophageal, gastro-esophageal, and cervical lesions.

The Materials and Methods used in the experiments presented in this example are now described.

Biopsies

Core or excisional biopsy specimens were placed directly into 2-ml screw-cap polypropylene tubes, each containing 750 μl of ice-cold acid-CH. The weight of the acid-containing tubes was recorded before and after addition of the biopsy specimen to determine the biopsy specimen mass. In the case of "far lung" samples, biopsies were obtained from sites distal to the tumor site in lung cancer patients. These samples comprise, presumably, non-malignant tissue. Similarly, samples obtained from Barretts pre-malignant lesions obtained from human patients comprise presumably non-malignant esophageal tissues. The samples were prepared and thiol measurements were performed as described previously herein in the Materials and Methods set forth in Example 1.

The Results of the experiments presented in this example are now described.

Elevated Cysteine Levels in Human Lung Lesions

Figure 4:
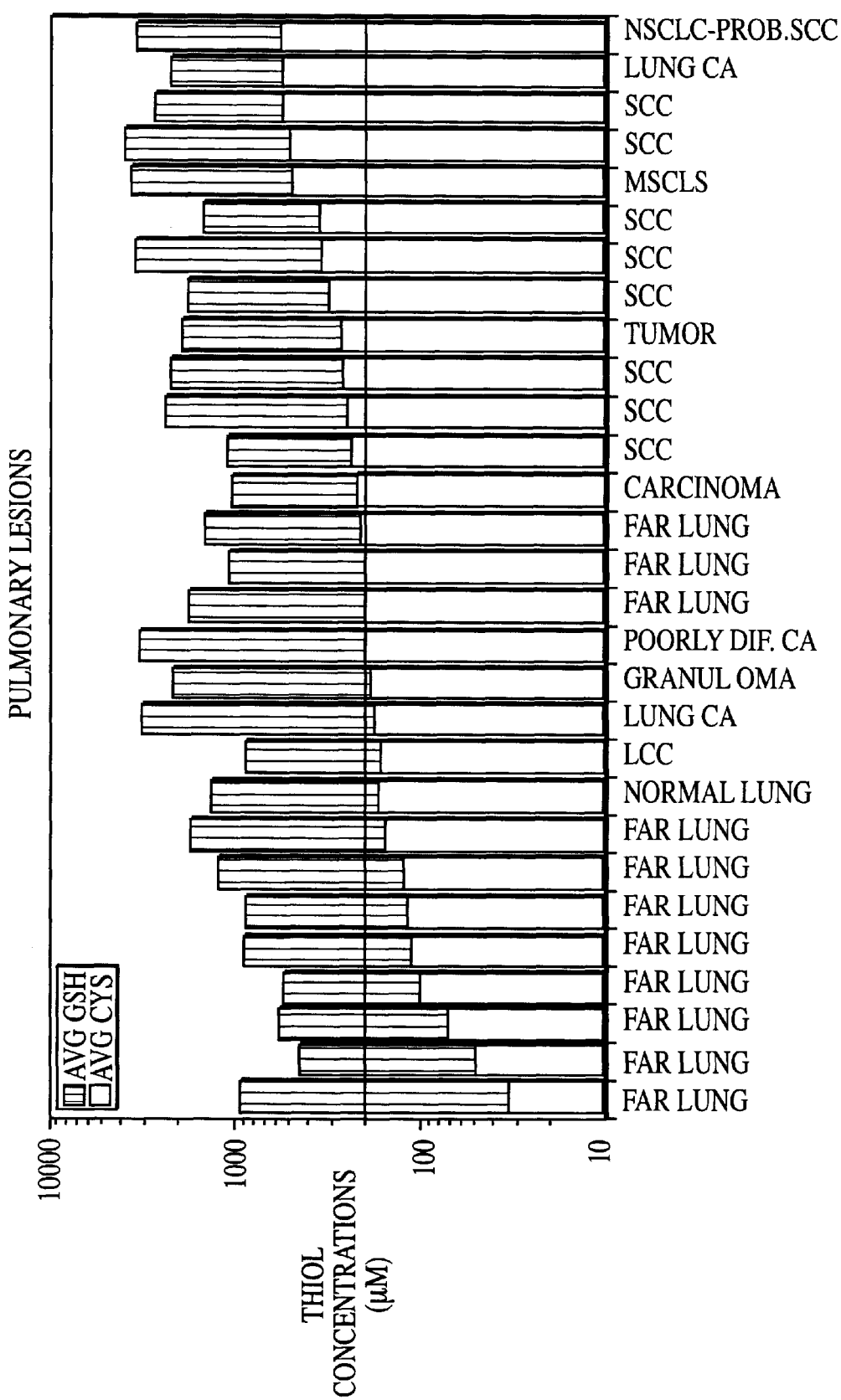
FIG. 4 is a graph depicting the concentration of free cysteine and glutathione in various human pulmonary lesions. Core or excisional biopsies were obtained from patients. The tissues were then processed and thiol measurements were obtained all as described elsewhere herein. The term "far lung" denotes a biopsy taken from a site distal to the lesion in a patient which site is, presumably, non-malignant. The line drawn at 200 $\mu$M separates almost all non-tumor (non-malignant) tissues from tumor (malignant) tissues with respect to the concentration of free cysteine (CYS) measured therein while no such line differentiating malignant from non-malignant human lung tissues can be drawn for glutathione levels (GSH). The abbreviations are as follows: CA, cancer; SCC, squamous cell carcinoma; and NSCLC, non-small cell lung cancer.

Biopsies from tumor and non-tumor lung tissues demonstrated elevated free cysteine concentrations in human lung tumors (FIG. 4). More importantly, the data disclosed herein demonstrate that a line differentiating tumor from non-tumor human lung tissue can be drawn at a free cysteine concentration of 200 μM with the concentration of free cysteine in non-tumor tissues falling below that level and the concentration in tumor tissues being above the 200 μM level. Further, lung tissue from sites distal to the tumor site, i.e., "far lung" samples, from lung cancer patients, which are considered to be non-malignant, consistently exhibited cysteine levels below 200 μM.

Additionally, no such line differentiating tumor from non-tumor tissue can be drawn for glutathione concentrations in human lung tissues. These results confirm the results obtained in rodent tumor cells described previously herein in Example 1. Therefore, human lung tumor tissues exhibit elevated free cysteine concentrations in vivo when compared with non-tumor lung tissues, and the lung tumor tissues typically demonstrate an absolute value, i.e., 200 μM, which is above the free cysteine concentration found in most, if not all, non-tumor tissues of the same origin.

Elevated Cysteine Levels in Human Esophageal and Gastro-esophageal Lesions

Figure 5:
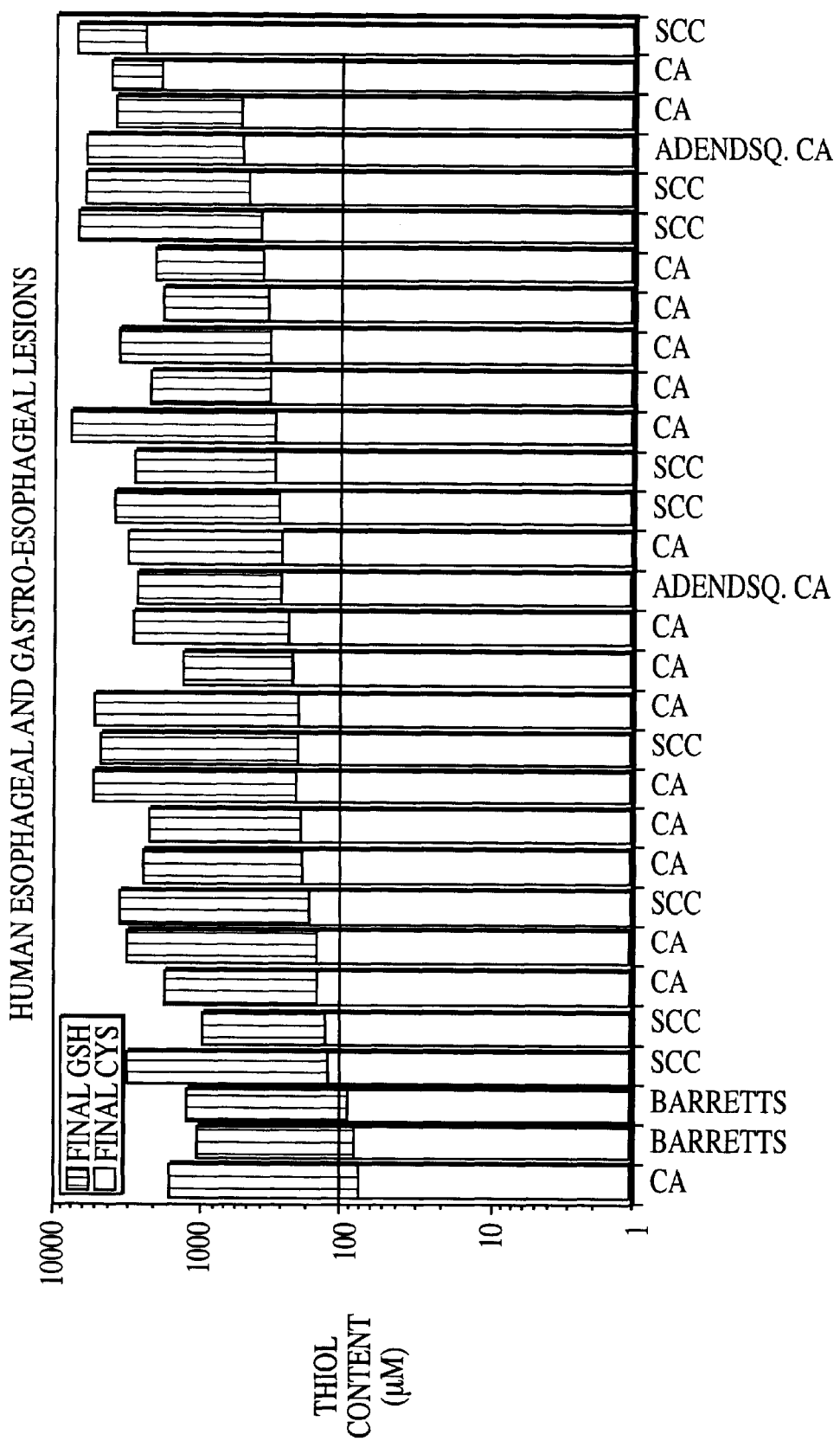
FIG. 5 is a graph depicting the concentration of free cysteine and glutathione in various human esophageal and gastro-esophageal lesions. Core or excisional biopsies were obtained from patients and the biopsies were placed in cold acid-CH as described elsewhere herein. The tissue samples were then processed and thiol measurements were obtained all as described elsewhere herein. The term "Barretts" refers to a non-tumor, pre-malignant condition which may be found in esophageal tissue. The line drawn at 100 $\mu$M separates almost all non-tumor (non-malignant) tissues from tumor (malignant) tissues with respect to the concentration of free cysteine (CYS) measured therein while no such line differentiating malignant from non-malignant human esophageal or gastro-esophageal tissues can be drawn for glutathione levels (GSH). The abbreviations are as follows: CA, cancer; SCC, squamous cell carcinoma; and ADENOSQ. CA, adenosquamous cancer.

Biopsies from tumor and non-tumor esophageal and gastro-esophageal tissues demonstrated the presence of elevated free cysteine concentrations in human lung tumors compared with non-tumor tissues of the same origin (FIG. 5). More importantly, the data disclosed herein demonstrate that a line differentiating tumor from non-tumor human esophageal and gastro-esophageal tissue can be drawn at a free cysteine concentration of 100 μM since the concentration of free cysteine in non-tumor tissues fell below that level and the concentration in most tumor tissues was above the 100 μM level. Moreover, the level of free cysteine found in tissues which are presumed to be non-tumor tissue but which are considered to be pre-malignant, i.e., Barretts, was also below the 100 μM level.

Further, no line differentiating tumor from non-tumor tissue can be drawn for glutathione concentrations in human esophageal and gastro-esophageal tissues confirming that there does not appear to be a correlation between glutathione levels and malignancy in mammalian tumors.

These data confirm the results obtained in rodent tumor cells described previously herein in Example 1. Therefore, human esophageal and gastro-esophageal tumor tissues exhibit elevated free cysteine concentrations in vivo when compared with non-tumor esophageal and gastro-esophageal tissues, and the tumor tissues typically demonstrate an absolute value, i.e., 100 µM, which is above the free cysteine concentration found in most, if not all, non-tumor tissues; of the same origin.

Elevated Cysteine Levels in Human Cervical Lesions

Figure 6:
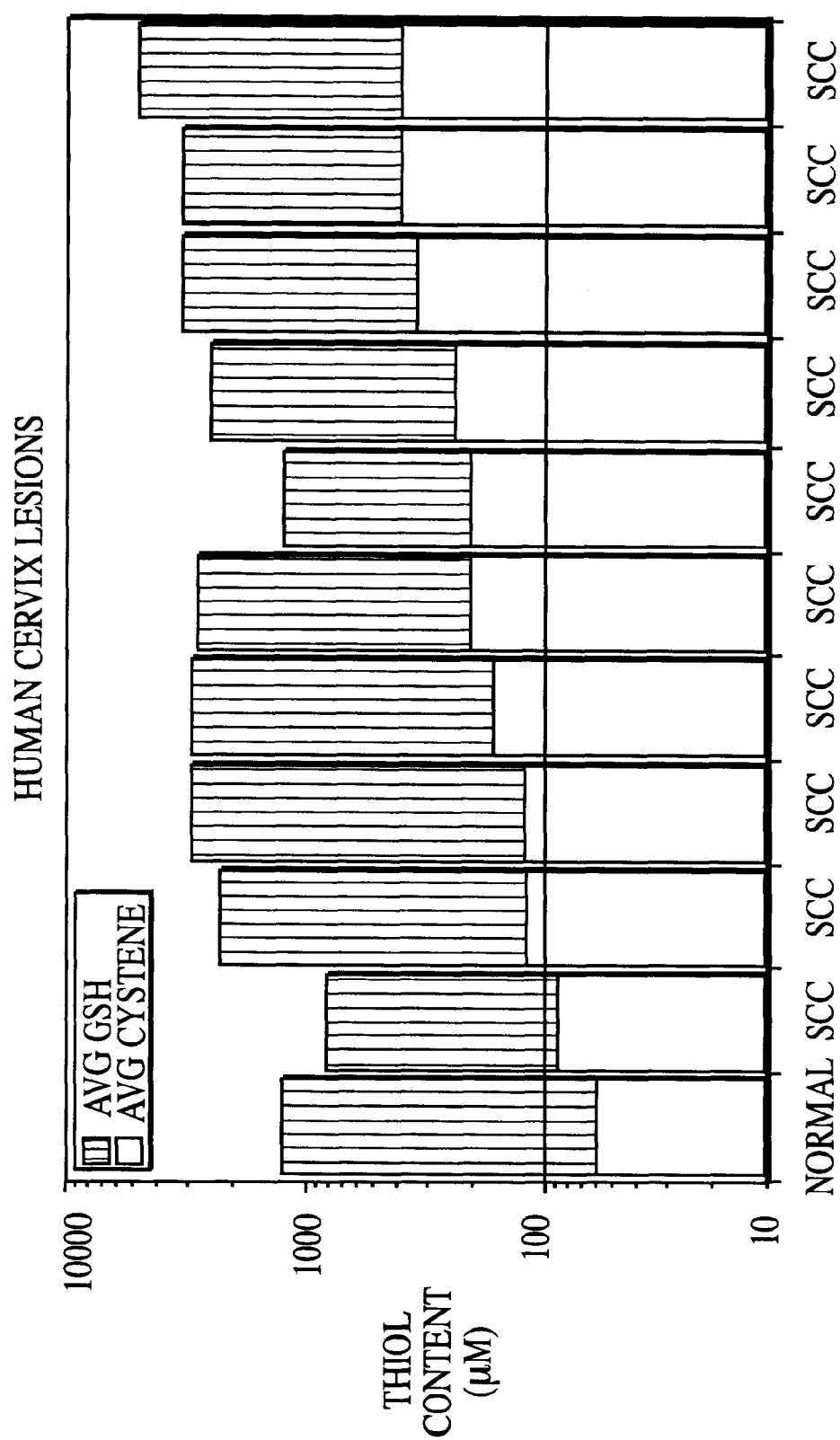
FIG. 6 is a graph depicting the concentration of free cysteine and glutathione in human cervical lesions. Core or excisional biopsies were obtained from patients and the biopsies were placed in cold acid-CH as described elsewhere herein. The tissue samples were then processed and thiol measurements were obtained all as described elsewhere herein. The line drawn at 100 $\mu$M separates almost all non-tumor (non-malignant) tissues from tumor (malignant) tissues with respect to the concentration of free cysteine (CYS) measured therein while no such line differentiating malignant from non-malignant human cervical tissues can be drawn for glutathione levels (GSH). The abbreviations are as follows: SCC, squamous cell carcinoma.

Biopsies from cervical tumor tissues demonstrated elevated free cysteine concentrations when compared with non-tumor tissues of the same origin (FIG. 6). More importantly, the data disclosed herein demonstrate that a line differentiating tumor from non-tumor human cervical tissue can be drawn at a free cysteine concentration of 100 µM with the concentration of free cysteine in non-tumor tissues falling below that level and the concentration in tumor tissues typically being above the 100 µM level.

Further, no line differentiating tumor from non-tumor tissue can be drawn for glutathione concentrations in human cervical tissues. These data confirm the findings in rodent tumor studies disclosed elsewhere herein in that there is no apparent correlation between glutathione concentration and malignancy.

Thus, these results confirm the data obtained from rodent tumor cells described previously herein in Example 1. Human cervical tumor tissues exhibit elevated free cysteine concentrations in vivo when compared with non-tumor cervical tissues, and the tumor tissues typically demonstrate an absolute value, i.e., 100 µM, which is above the free cysteine concentration found in most, if not all, non-tumor tissues of the same origin.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting a tumor in a human tissue, the method comprising measuring the concentration of free cysteine in the tissue, wherein a concentration higher than about 80 micromolar is an indication that the tissue bears a tumor.

2. The method of claim 1, wherein the tissue is selected from the group consisting of lung tissue, esophageal tissue, gastro-esophageal tissue, and cervical tissue.

3. The method of claim 2, wherein the tissue is lung tissue and further wherein a concentration higher than about 200 micromolar is an indication that the tissue bears a tumor.

4. The method of claim 2, wherein the tissue is esophageal tissue and further wherein a concentration higher than about 100 micromolar is an indication that the tissue bears a tumor.

5. The method of claim 2, wherein the tissue is gastro-esophogeal tissue and further wherein a concentration higher than about 100 micromolar is an indication that the tissue bears a tumor.

6. The method of claim 2, wherein the tissue is cervical tissue and further wherein a concentration higher than about 100 micromolar is an indication that the tissue bears a tumor.

7. The method of claim 1, wherein the concentration is measured by suspending a sample of the tissue in cold acid and measuring the concentration if free cysteine in the cold acid.

8. The method of claim 7, wherein the sample is suspended in the cold acid for at least about 10 minutes before measuring the concentration of free cysteine in the cold acid.

9. The method of claim 7, wherein the concentration of free cysteine in the cold acid is measured by liquid chromatography.

10. The method of claim 7, wherein the sample is homogenized in the cold acid before measuring the concentration of free cysteine therein.

11. The method of claim 7, wherein the cold acid is centrifuged before measuring the concentration of free cysteine therein.

12. The method of claim 7, wherein the cold acid comprises a chelator.

13. The method of claim 12, wherein the chelator is selected from the group consisting of ethylenediaminetetraaceteic acid, diethylenetriaminepentaacetic acid, and diethyldithiocarbamate.

14. The method of claim 7, wherein the cold acid comprises sulfosalicylic acid.

15. The method of claim 7, wherein the cold acid has a temperature of not more than 4 degrees Celsius.

16. A method of assessing the effect of an antitumor therapy on a tumor in a human tissue, the method comprising comparing the concentration of free cysteine in the tumor before the antitumor therapy and the concentration of free cysteine in the tumor during or after the antitumor therapy, whereby a lower concentration of free cysteine in the tumor during or after the antitumor therapy indicates that the antitumor therapy decreases at least one of the size, the rate of growth, and metastasis of the tumor.

17. The method of claim 16, wherein the antitumor therapy is selected from the group consisting of chemotherapy and radiation therapy.

18. The method of claim 16, wherein the concentration of free cysteine in the tumor is measured by suspending a sample of the tissue in cold acid and measuring the concentration of free cysteine in the cold acid.

19. The method of claim 18, wherein the sample is suspended in the cold acid for at least about 10 minutes before measuring the concentration of free cysteine in the cold acid.

20. The method of claim 18, wherein the concentration of free cysteine in the cold acid is measured by liquid chromatography.

21. The method of claim 18, wherein the sample is homogenized in the cold acid before measuring the concentration of free cysteine therein.

22. The method of claim 18, wherein the cold acid is centrifuged before measuring the concentration of free cysteine therein.

23. The method of claim 18, wherein the cold acid comprises a chelator.

24. The method of claim 23, wherein the chelator is selected from the group consisting of ethylenediaminetetraaceteic acid, diethylenetriaminepentaacetic acid, and diethyldithiocarbamate.

25. The method of claim 18, wherein the cold acid comprises sulfosalicylic acid.

26. The method of claim 18, wherein the cold acid has a temperature of not more than 4 degrees Celsius.

27. A method of assessing the resistance of a human tumor cell to an antitumor therapy, the method comprising comparing the concentration of free cysteine in the tumor cell and the concentration of free cysteine in a non-tumor cell of a tissue of the same type, whereby a higher concentration in the tumor cell than in the non-tumor cell is an indication that the tumor cell is more resistant to the antitumor therapy than the non-tumor cell.

28. The method of claim 27, wherein the tumor cell is in a tumor.

29. The method of claim 27, wherein the antitumor therapy is selected from the group consisting of chemotherapy and radiation therapy.

30. The method of claim 29, wherein the antitumor therapy is radiation therapy.

* * * * *